US010101209B2

(12) United States Patent
Selker et al.

(10) Patent No.: US 10,101,209 B2
(45) Date of Patent: Oct. 16, 2018

(54) METHOD AND APPARATUS FOR QUANTIFYING SOLUTIONS COMPRISED OF MULTIPLE ANALYTES

(75) Inventors: Mark Selker, Los Altos Hills, CA (US); Barbara Paldus, Woodside, CA (US)

(73) Assignee: Finesse Solutions, Inc., Carlsbad, CA (US)

( * ) Notice: Subject to any disclaimer, the term of this patent is extended or adjusted under 35 U.S.C. 154(b) by 782 days.

(21) Appl. No.: 13/506,585

(22) Filed: Apr. 30, 2012

(65) Prior Publication Data
US 2013/0286380 A1 Oct. 31, 2013

(51) Int. Cl.
| | |
|---|---|
| *G01J 3/44* | (2006.01) |
| *G01N 21/65* | (2006.01) |
| *G01J 3/02* | (2006.01) |
| *G02B 6/02* | (2006.01) |

(52) U.S. Cl.
CPC ............... *G01J 3/44* (2013.01); *G01J 3/0218* (2013.01); *G01N 21/65* (2013.01); *G02B 6/02385* (2013.01); *G01N 2201/08* (2013.01); *G01N 2201/129* (2013.01); *G02B 6/02328* (2013.01)

(58) Field of Classification Search
CPC ...... G01J 3/44; G01J 3/00; G01J 1/00; G01N 21/00; G01N 21/47; G01N 21/65; G01N 33/53; C12M 1/34; G02B 6/02
USPC ....... 356/51, 301; 250/283; 435/6.11, 288.7; 385/15
See application file for complete search history.

(56) References Cited

U.S. PATENT DOCUMENTS

| | | | |
|---|---|---|---|
| 4,784,486 A | 11/1988 | Van Wagenen et al. | |
| 5,786,893 A | 7/1998 | Fink et al. | |
| 5,870,188 A * | 2/1999 | Ozaki et al. | 356/301 |
| 2003/0231305 A1* | 12/2003 | Zeng | 356/301 |
| 2009/0252452 A1* | 10/2009 | Taru et al. | 385/15 |
| 2010/0007876 A1* | 1/2010 | Chen et al. | 356/301 |
| 2010/0059673 A1* | 3/2010 | Makarov et al. | 250/283 |
| 2010/0203549 A1* | 8/2010 | Petricoin et al. | 435/7.1 |

(Continued)

FOREIGN PATENT DOCUMENTS

| | | |
|---|---|---|
| EP | 0764844 | 3/1997 |
| WO | 2009/128995 | 10/2009 |

OTHER PUBLICATIONS

Yun Han, et al. Liquid-Core Photonic Crystal Fiber Platform for Raman Scattering Measurements of Microliter Analyte Solutions Proc. of SPIE vol. 6767 pp. 1-8.

(Continued)

*Primary Examiner* — Jamil Ahmed

(57) ABSTRACT

A multi-analyte sensor system based on hollow core photonic bandgap fiber and Raman anti-Stokes spectroscopy. The system includes:
  i) an inlet to introduce an analyte sample into an analyzer chamber which analyzer includes;
  ii) a measurement system to derive the anti-Stokes spectral peaks and/or spectra of the sample;
  iii) a set of reference calibrants corresponding to the analytes of which the sample is primarily comprised;
  iv) a second inlet to introduce said calibrants into the analyzer chamber;
  v) a second measurement system to derive the anti-Stokes spectral peaks and/or spectra of the calibrants
  vi) an outlet through which the sample and calibrants are expelled from the analyzer chamber.

41 Claims, 13 Drawing Sheets

(56) References Cited

U.S. PATENT DOCUMENTS

| | | | |
|---|---|---|---|
| 2011/0267612 A1* | 11/2011 | Roberts et al. | 356/301 |
| 2011/0299065 A1* | 12/2011 | Loebig et al. | 356/51 |
| 2012/0123688 A1* | 5/2012 | Ramasubramanyan et al. | 702/19 |
| 2012/0135405 A1* | 5/2012 | Toumbas et al. | 435/6.11 |
| 2012/0244609 A1* | 9/2012 | Selker et al. | 435/288.7 |

OTHER PUBLICATIONS

Chao Shi et al. Low Concentration Biomolecular Detection Using Liquid Core Photonic Crystal Fiber Proc. of SPIE vol. 685204 pp. 1-8.

Felicity Cox et al. Surface Enhanced Raman Scattering in a Hollow Core Microstructered Optical Fiber Optics Express vol. 15,No. 21 p. 13675-81.

European Partial Search Report dated Dec. 5, 2013 issued in EP 13 165 611.8.

Dou, X., et al., "Biological applications of anti-stokes Raman spectroscopy: quantitative analysis of glucose in plasma and serum by a highly sensitive multichannel Raman spectrometer," Applied Spectroscopy, vol. 50, No. 10, 1996, pp. 1301-1306.

Yamamoto, H., et al., "Quantitative analysis of metabolic gases by multichannel Raman spectroscopy: use of a newly designed elliptic-spherical integration type of cell holder," Applied Optics, vol. 37, No. 13, May 1, 1998, pp. 2640-2645.

Enejder, A. M. K., et al., "Blood analysis by Raman spectroscopy," Optics Letters, vol. 27, No. 22, Nov. 15, 2002, pp. 2004-2006.

Berger, A., et al., "Multicomponent blood analysis by near-infrared Raman spectroscopy," Applied Optics, vol. 38, No. 13, May 1, 1999, pp. 2916-2926.

* cited by examiner

METHOD AND APPARATUS FOR QUANTIFYING SOLUTIONS COMPRISED OF MULTIPLE ANALYTES

BACKGROUND OF THE INVENTION

The search for an accurate, at-line real time multi-analyte analyzer has been ongoing for many years. The application space for such an analyzer is both diverse and broad, spanning many fields including but not limited to food and beverage manufacture, medical diagnostics, chemical analysis, energy, and especially bio-processing and bio-technology. While the description of the present invention focuses mainly on biotechnology based applications, the invention described and claimed and the principles discussed in respect thereto are general in applicability and the conclusions are not limited to the biotechnology application arena.

The demand for this type of analyzer instrument in many fields is based on the need to quantitatively analyze multiple analyte species present within a sample in a closed container. Numerous attempts have been made to apply a wide variety of technologies for this purpose. While instruments exist today that invasively take samples which are then analyzed using standard chemical assays in a more or less automated format, the preferred analytical solution would be non-invasive and therefore not require a breach in the wall of the sample container. Some of the most often applied technologies to achieve sample analysis are so-called "label free" optical technologies that probe the system under test. These techniques are minimally invasive although not actually non-invasive and hold the promise of not compromising either the test sample or the system under test.

Linear scatter and absorption based optical analytical techniques have to date proved to be of only limited use, as they either lack specificity or require some tag or label to be introduced into the sample, thereby contaminating it and making it unavailable for further use. Early attempts using optics often employed near-infrared (NIR) absorption to measure spectral signatures in order to uniquely identify and quantify the analytes of interest (see *Simultaneous Measurement of Glucose and in Insect Cell Media Culture by Near Infrared Spectroscopy*, Riley et al, Biotechnology and Bioengineering, 55, 1, p. 11, 1997 and *Determination of physiological levels of glucose in an aqueous matrix with digitally filtered Fourier transform near-infrared spectra*, M. A. Arnold and G. W. Small, Anal. Chem. 62, p. 145, 1990). Attempts to quantify biological materials using NIR (near infra-red) spectroscopy generally fail due to the lack of specificity provided by this type of spectroscopy. The spectral features found in the NIR are generally not particularly sharp (narrow) or distinct, thereby making it difficult to recognize the spectral features, and extract individual analyte concentrations owing to spectral overlap. Specifically, when many analytes are present simultaneously, it is difficult if not impossible even using sophisticated multi-variate computer-based algorithms to obtain clinically accurate results. Additionally, any system noise compromises the spectral data as the broad and rolling spectral features overlap and are smeared out. Even determining the exact spectral peak locations and amplitudes can often be extremely challenging.

More recent spectroscopic investigations have utilized the Raman scattering effect to interrogate the sample, as Raman spectra are generally sharper and more distinct (see *Concentration Measurements of Multiple Analytes in Human Sera by Near-Infrared Laser Raman Spectroscopy* Jianan Y. Qu, Brian C. Wilson, and David Suria, Applied Optics, 38, 25, p. 5491, 1999 and *Rapid, noninvasive concentration measurements of aqueous biological analytes by near-infrared Raman spectroscopy*, Andrew J. Berger, Yang Wang, and Michael S. Feld, Applied Optics, Vol. 35, 1, p. 209, 1996). Raman scattering is a known nonlinear optical scattering process which involves inelastic scattering of a photon and an atom or molecule. When light is scattered from an atom or molecule, most photons are elastically scattered such that the scattered photons have the same energy and wavelength (frequency) as the incident photons (i.e., Rayleigh scattering). However, a small fraction of the scattered photons have a frequency different from the frequency of the incident photons. This new frequency can be higher and/or lower, but the scattering to the lower energy level occurs with a far higher probability per unit time. For this inelastic scattering process to proceed, the energy (and momentum) difference is taken up by the atom or molecule in a process whereby an electronic, vibrational, or rotational quantum is excited and/or de-excited.

The inelastic scattering process known as the Raman Effect leads to both lower and higher energy scattered photons, which are referred to as Stokes scattering and anti-Stokes scattering, respectively. The Raman Effect is often modeled as the absorption and subsequent re-emission of a photon via an intermediate vibrational state, having a virtual energy level. If/when this absorption and re-emission of light occurs in Raman scattering there is an energy exchange between the incident photons and the molecules. The energy differences are equal to the difference in the electrical, vibrational or rotational energy-levels of the atom/molecule. In Raman spectroscopy of molecules, the vibrational energy shift is the most commonly observed. If a molecule absorbs energy and a lower energy photon is emitted, it is referred to as Stokes scattering. The resulting photons of lower energy have an energy distribution which generates a Stokes spectrum that is "red-shifted" from the incident beam, or equivalently stated, lower in energy than the pump light. If the molecule loses energy (gives up a quantum unit of energy from an excited electronic, vibrational, or rotational state) by having that energy combine with an incident photon, it is referred to as anti-Stokes scattering. These incident photons are shifted to the higher energy (blue) side of the incident light These differences in energy between incident and scattered photons are measured by subtracting the energy of the single-frequency excitation laser light source from the energy of the inelastically scattered photons. The intensities of the Raman bands are dependent on the number of molecules occupying the different vibrational states, when the process began. If the sample is in thermal equilibrium, the relative numbers of molecules in states of different energy will be given by the Boltzmann distribution:

$$\frac{N_1}{N_0} = \frac{g_1}{g_0} e^{-\frac{\Delta E_v}{kT}}$$

where:
  $N_0$: number of atoms the lower vibrational state
  $N_1$: number of atoms in higher vibrational state
  $g_0$: degeneracy of the lower vibrational state
  $g_1$: degeneracy of the higher vibrational state
  $\Delta E_v$: energy difference between these two vibrational states
  k: Boltzmann constant
  T: temperature Kelvin It can be seen from the Boltzmann relationship shown above that lower energy states will be more highly occupied than the higher energy states. Therefore, the Stokes spectrum will be significantly more intense than the anti-Stokes spectrum generally by a few orders of magnitude. Given that the spontaneous Stokes signal is orders of magnitude lower in power than the incident light, the spontaneous anti-Stokes signal in most free space optical systems will be very close in amplitude to the noise floor of the measurement system. Additionally, the scattered light will be Lambertian and therefore the capture of the scattered light for analysis will be limited by a restatement of the $2^{nd}$ law of thermodynamics known as conservation of brightness (see *Art of Radiometry*, James Palmer and Barbara Grant, 2010 SPIE, ISBN 978-0-8194-7245-8). It is for this reason that the anti-Stokes spectrum has typically not been of common or practical use in analyte detection and identification.

The most commonly employed Raman spectroscopy system for analyte identification of biological samples is a Raman Stokes system that uses a laser source having a wavelength of 785 or 830 nm. The excitation wavelength can be anywhere from the ultra violet to the infrared, but the most common wavelengths employed are between 700 nm-900 nm (near infrared or NIR) window because laser sources of this wavelength are readily available and most tissue and biological fluids exhibit minimum absorption in this wavelength region so that auto-fluorescence (which results in a non-uniform baseline shift interference) is reduced. These advantages of the NIR pump region are counter balanced by two limitations:

1. The Raman Stokes scattering cross section, (hence signal intensity) has a $1/\lambda^4$ dependence, where $\lambda$ here represents the wavelength of the excitation source;
2. The sensitivity of the most common multi-channel detectors used in conjunction with NIR optical spectrometers, namely silicon CCDs (charge coupled devices), falls off rapidly for wavelengths exceeding 1 µm.

Therefore, in the 785 to 830 nm wavelength regime there is a local optimum that can be achieved by a tradeoff between Raman cross-section, auto-fluorescence, detector sensitivity, and filter efficiency. Systems are employed at other wavelengths depending on situation and the wavelength dependence of the Raman cross-section, or if resonance Raman scattering is utilized (see *Achievements in resonance Raman spectroscopy: Review of a technique with a distinct analytical chemistry potential*, Evtim V. Efremov, Freek Ariese, Cees Gooijer, Analytica Chimica Acta, Volume 606, Issue 2, 14 Jan. 2008, Pages 119-134). This depends on which part of the atomic or molecular (electronic, rotational, vibrational) spectrum which is intended to be probed, as well as the complexity and molecular structure of the analyte species and background matrix being measured.

In practice, art workers implementing optical free space spontaneous Raman spectroscopy systems have generally utilized a carefully designed free space optical system (bulk lenses, reflecting collection systems, or the like) to collect the Raman Stokes scattered light. As previously mentioned, given that the Raman scattered light generally constitutes what is known as a Lambertian source the detection system collection efficiency and coupling to the spectrometer will be limited by the law of the conservation of brightness (see *Art of Radiometry*, James Palmer and Barbara Grant, 2010 SPIE, ISBN 978-0-8194-7245-8).

The existing body of scientific literature contains descriptions of numerous systems for analyte identification and quantification based on Raman spectroscopy systems. A bio-analysis system was described by Berger et al (*Multicomponent Blood Analysis by Near-Infrared Raman Spectroscopy*, Andrew J. Berger, Tae-Woong Koo, Irving Itzkan, Gary Horowitz, and Michael S. Feld, Applied Optics, 38, 13, p. 2916, 1999). This particular system was designed to non-invasively measure analytes of medical significance in human blood (e.g.: Glucose, Cholesterol, Triglyceride, Urea, Total Protein, and Albumin). The apparatus utilized a diode laser emitting at 830 nm, a mirror and lens system to collect the Raman Stokes light and deliver it to a spectrometer that employed a silicon CCD array. This system reportedly yielded quantitative results that approached the accuracy required to be used in clinical measurements. Given that the Raman Stokes scattered light levels were low and that they were going through a turbid media (skin and blood), Berger at al. used the method of Partial Least Squares (PLS) and training sets in order to retrieve the concentration data from the spectral data of multiple analytes simultaneously (see *Multivariate Calibration*, H. Martens and T. Naes, Wiley, New York, 1989 or *Mixture analysis of spectral data by multivariate methods*, or Windig, W., Chemom. Intell. Lab. Syst. 4, p. 201-213, 1988). Training sets are the response function spectra of the instrument to a known set of analytes with known concentrations. These training sets are required so that the PLS algorithm can create a set of basis vectors that are then used computationally to determine the concentrations of multiple analytes in a given sample's Raman Stokes spectrum. This sample's total spectrum is comprised of the spectra of each of the individual analytes hitting the detector simultaneously and with the relative amplitudes of each individual component of the spectrum determined by their concentration, Raman cross section, the pump light amplitude, and scattering at the respective wavelengths comprising the spectrum. If the conditions change such that the training sets are no longer valid (e.g., as a result of the addition of other spectral components or a change in the spectral baseline), then the results gained using PLS may no longer be correct. This can occur for instance in a biological sample if there is spectral content added due to a bacterial infection, or if the sample is modified in a way that changes the basis vectors of the training set. Multivariate analysis techniques like PLS are also sensitive to changes in both the signal and/or the training sets, and quantitation errors can creep in due to noise or other effects that impact either the signal integrity or the training sets. Also, training sets are in general both time-consuming and can sometimes be difficult to create. Finally, if anything changes the nature of the system by changing the constituent make up or composition, the training sets may no longer be valid, thereby invalidating the basis vectors and signals. For example, such a situation can easily be envisaged in biological systems where an adventitious agent (bacterial of viral) can change the chemical make-up of a system or in chemical systems where dyes or additives can clearly change the absorption profiles of the system.

Another complication for this type of system, and indeed for almost all optical systems including Raman spectroscopy systems used to measure biological samples, is fluorescence. As both the Raman Stokes signal and auto-fluorescence emissions are red-shifted from the pump light, there is always overlap between the two signals. This complicates the detection and identification process as the fluorescence emission often obfuscates the Raman Stokes spectrum. A known technique to try and mitigate the effects of auto-fluorescence is to fit it to a high order polynomial (typically $5^{th}$ order) and subtract it out of the spectrum (see *Automated*

Method for Subtraction of Fluorescence from Biological Raman Spectra, Lieber and Mahadevan-Jansen, Applied Spectroscopy, 57, 11, p. 1363, 2003). While this technique aids in cleaning up the spectrum, it is not obvious that all of the auto-fluorescence is accurately fitted and that the amplitudes of the spectral features that are revealed are absolutely or even relatively correct. A published example of this fitting and subtraction technique is shown in FIG. 1 (see *Quantitative analysis of serum and serum ultrafiltrate by means of Raman spectroscopy*, Rohleder et al, Analyist, 129, p. 906, 2004). While the peaks are more visibly revealed, there is no evidence that the amplitudes of all the features have been maintained in true proportion thereby leading to the potential for quantitation errors when used in conjunction with multi-variate analysis.

Clearly, if the Raman Stokes signal can be increased relative to the fluorescence background, many of these issues can be mitigated. However, the Raman Stokes signal and the fluorescence signal both vary linearly with the intensity of the pump light so it is difficult to preferentially generate a Stokes signal with higher relative amplitude to the fluorescence. The act of subtracting off a generic function as described above can often be the mathematical operation of subtracting signals of similar magnitude and thereby offers little improvement in the signal to noise ratio and adds uncertainty to the resulting spectrum. However, in samples that are first passed through a filtration/optical scattering particle reduction system (e.g.: ultrafiltration, centrifugation etc.) the increased Raman Stokes amplitude can result in higher signal to noise ratios as the filtering reduces the auto-fluorescence and scattering losses (see *Quantitative analysis of serum and serum ultrafiltrate by means of Raman spectroscopy*, Rohleder et al., 129, p. 906, Analyst, 2004). Despite these facts, many attempts have been made to increase the Raman signal including using higher power pump lasers, and increasing the density of the target analyte. Some approaches have generally utilized clever optical systems to preferentially capture more of the Raman Stokes scattered signal light.

Hollow waveguide technology is one method for increasing the Raman Stokes signal that holds promise. The use of hollow core Teflon AF® tubing as an optical waveguide was met with great interest when first demonstrated by Altkorn (see *Low-loss liquid-core optical fiber for low refractive index liquids: fabrication, characterization, and application in Raman spectroscopy*, Alkorn et al, Applied Optics, 36, 34, p. 8992, 1997). Teflon AF is one of the few materials with a refractive index lower (n~1.29) than many aqueous solutions ($n_{water}$~1.33) a property that allows it to serve as an optical waveguide. This fact allows many aqueous solutions to be analyzed using Raman spectroscopy by introducing the solution into the hollow core Teflon AF waveguide. The increased confinement in the core and increased interaction length both act to enhance the Raman signal. Specifically, the Teflon tubing acts as a waveguide as the pump rays introduced into the core and the Raman Stokes signal generated in the core undergo total internal reflection at the liquid/Teflon boundary and are thereby confined primarily within the core. This results in an increased interaction path and a higher level of intensity over this path than a comparable free space system. Increases in the sensitivity of the system by a factor of 500 have been reported, though the general enhancement factor that can be achieved is correlated to the exact experimental geometry implemented (see *Intensity Considerations in Liquid Core Optical Fiber Raman Spectroscopy*, Altkorn et al, Applied Spectroscopy, 55, 4, p. 373, 2001 and *Raman Sensitivity Enhancement for Aqueous Protein Samples Using a Liquid-Core Optical-Fiber Cell*, M. J. Pelletier and Altkorn, Anal. Chem., 73 (6), pp 1393-1397, 2001)

Unfortunately, small diameter (sub 100 micron inner-diameter) Teflon capillary tubing is not readily available and it is therefore difficult to make a single mode waveguide in the near-infrared spectral region. This is because the number of propagating modes in this type of waveguide is dependent on the product of the ratio of the core diameter to the wavelength and the square root of the difference between the squares of the core refractive index and cladding refractive index. Often with the case of Teflon waveguides, the waveguide diameter approaches a level where it is two orders of magnitude larger than the wavelength of the light propagating so that the mode picture is replaced by a ray optics and numerical aperture description of the light propagation within the tube (see *Intensity Considerations in Liquid Core Optical Fiber Raman Spectroscopy*, Altkorn et al, Applied Spectroscopy, 55, 4, p. 373, 2001). Moreover Teflon materials can be difficult to work with as the low surface tension does not allow them to readily bond with other materials. The larger diameter tubing used in the literature has resulted in waveguides that are not single mode for either NIR pump wavelengths or the Raman signal. The fact that the waveguide is multi-spatial mode allows the pump and the Raman Stokes signal to have different spatial profiles and effective velocities in the waveguide thereby limiting the integrated spatial overlap and overall conversion efficiency from the pump to the Raman Stokes signal. Additionally, as Teflon is difficult to bond to, the coupling of the light and fluid into and out of the fiber is usually accomplished using mechanical fixturing (as opposed to an integrated set of bonded components) which can be cumbersome to implement. Finally, there are fundamental limitations to the density of materials that can be analyzed with Teflon tubing, as the refractive index of the material approaches that of the Teflon cladding.

Another impediment to accurate quantification in the identification of biological or other types of samples with optical analyzers based on Raman scattering is the linear optical loss caused by particles in the sample and/or absorption of the pump or the Raman scattered light by the sample. For instance, in whole blood, there is both absorption and scattering in the NIR. The blood cells can create large scattering losses and the Raman Stokes levels can be mediated by direct scattering of the Raman Stokes signal and/or by pump light scattering as well as by pump light and/or signal absorption. The effect of absorption or scattering loss can be accounted for if the magnitude of the loss coefficient is known, but this is often very difficult to determine a priori. Although one can devise an instrument to measure the loss coefficients in-situ the overall instrument set-up becomes quite complicated and therefore impractical to employ commercially. An example of a laboratory system where this has been implemented is shown in FIG. 3 (see *Chemical concentration measurement in blood serum and urine samples using liquid-core optical fiber Raman Spectroscopy*, Qi and Berger, Applied Optics, 46, 10, p. 1726, 2007). Here a Raman Stokes analyzer using a Teflon AF waveguide and simultaneously employed a white light spectrometer to account for the scattering and absorption in the sample along the waveguide path. The authors here also reported viable results using this system, but required integration times in excess of 10 seconds despite the waveguide enhancement and the compensation for optical losses.

Some of the aforementioned issues with Teflon based hollow core fibers have been somewhat overcome with the advent of hollow core photonic band-gap (HCPBG) fibers (see *Photonic Crystal Fiber*, Philip Russell, Science 17, 299, 5605, p. 358, 2003, U.S. Pat. No. 6,829,421, Hollow Core Photonic Bandgap Optical Fiber, and Published US Patent Application 2006/0062533, Photonic Crystal Fiber, Method of Manufacturing the Crystal Fiber and Method of Connecting the Fiber). The nature of the photonic band-gap allows most gases or liquids to be confined in the core of the fiber, while guiding of the excitation (pump) and scattered (signal) light is supported. Additionally, it allows for the fiber to be constructed so that the sample of interest is introduced into the core but the fiber remains single mode or close to single mode for both the pump light and the emitted spectra in the near infrared spectral region. Several groups have implemented Raman Stokes analyzers using HCPBG fiber and others have explored various systems and concepts using this type of fiber (see Published US Patent Application 2010/0014077, U.S. Pat. No. 7,595,882, *Stimulated Raman scattering in an ethanol core microstructured optical fiber*, Yiou et al, Optics Express, 13, 12, p. 4786, 2005, and *Determination of Ethanol Concentration by Raman Spectroscopy in Liquid-Core Microstructured Optical Fiber*, Meneghini et al, IEEE Sensors Journal, 8, 7, p. 1250, 2008). U.S. Pat. No. 7,595,882 describes a system for identifying homo-nuclear molecules confined to the core of HCPBG fibers. This patent describes the general advantages provided by confining the radiation and the sample to a hollow core. Published US Patent Application 2010/0014077 describes a method for identifying biological samples using HCPBG as a Raman biosensor. In addition to a general description of how to use the Raman Stokes signal to create a bio-analyzer, this patent application discusses how to pick the fiber core diameter or the wavelength of the pump light for a given fiber design and a given analyte mixture's index of refraction based on a published reference. If a commercially available HCPBG fiber comes in specific discrete core diameters, the single-mode cut-off wavelength is determined for a given index of refraction media in the hollow-core based on the photonic band gap cladding. The above-cited patent application focuses solely on Raman Stokes signals as indicated by the spectra shown with a positive wavelength shift and makes no mention of an anti-Stokes spectrum. We have found that stimulated Raman anti-Stokes based spectroscopy is also possible with HCPBG fiber. The first stimulated Raman anti-Stokes signal will occur when there is a large enough population build-up in the first Raman Stokes and Raman anti-Stokes levels to allow for this process.

Recent work was performed by Meneghini et al. (see *Determination of Ethanol Concentration by Raman Spectroscopy in Liquid-Core Microstructured Optical Fiber*, Meneghini et al, IEEE Sensors Journal, 8, 7, p. 1250, 2008). Here a HCPBG fiber was used to determine ethanol and sucrose content in a set of samples. In the described system, the HCPBG fiber was spliced to multi-mode fiber on both the input and output ends so that pump light could be coupled in and Raman Stokes light could be coupled out and sent to a spectrometer. The input and output fibers were attached to the HCPBG fiber using a fusion splicer. The act of fusion splicing also collapsed the cladding holes around the launch (light input) area. Additionally, laser holes were drilled into the side of the fiber allowing the core to be filled with the ethanol and sucrose containing solutions that comprised the samples under test. The system reportedly gave clean and well resolved Raman Stokes spectra, thereby allowing for reasonably accurate quantification of the analyte concentrations using univariate techniques. Spectral graphs were obtained with 1 mW and 1 meter of HCPBG fiber as there was no fluorescence to complicate the spectrum and little scattering. Their testing, however, did not involve biological samples and/or any samples having large fluorescence and/or scattering/absorptive backgrounds. Additionally, it was clear from their work that very low pump laser powers (<10 mW) and very short fibers (<2 M) were required to get their results.

It is important to note that while all of the previously referenced prior art refers to "Raman scattering", the term was invariably used solely in the context of the Raman Stokes spectrum The only reported work known to the present inventors which addresses identifying analytes using the Raman anti-Stokes spectrum is described in *Biological Applications of Anti-Stokes Raman Spectroscopy: Quantitative Analysis of Glucose in Plasma and Serum by Highly Sensitive Multichannel Raman Spectrometer*, Dou et al, Applied Spectroscopy, 50, 10, p. 1301, 1996. It was reported by Dou et al, that by employing the complex free space optical collection system they utilized, the anti-Stokes spectrum could be used to predict the concentration of glucose in blood serum if their collection system was implemented. Their optical collection system (as shown in FIG. 3) consisted of a quartz flow cell surrounded by a gold coated integrating ellipse (it collects or integrates the signal) with two holes in it, one small hole 310 that allowed the Argon Ion pump laser light to pass into the cell, and a small conically shaped hole 320 through which the anti-Stokes spectrum escaped and was subsequently collimated and sent to a holographic spectrometer and CCD array. The elliptical chamber 315 was designed to optimize the Raman anti-Stokes signal emanating from the quartz flow cell 300. Given the very short interaction length of the pump and the analyte and the fact that the spontaneous Raman anti-Stokes signal is emitted into all space, efficient generation and collection of the signal is very challenging. Despite their carefully designed and implemented free space collection system, they still required 100 mW of pump power at 5145 nm and also needed to integrate on their CCD for 3 seconds to obtain reasonably clear spectra. Also, they simultaneously collected both the Stokes and anti-Stokes spectrum in the presence of heavy fluorescence of the plasma (as shown in FIG. 4). Using the Raman anti-Stokes band at 1130 cm$^{-1}$ they were able to create a plot of glucose concentration in blood plasma that matched the intensity on the CCD with a correlation coefficient of 0.993; as is shown in FIG. 5. They apparently did not require multivariate analysis/PLS and/or training sets in order to determine the concentration of the analyte that was varied. However, it should be noted that if multiple target analytes are present, there is significant potential for "interferences" (i.e. overlaps between the Raman anti-Stokes spectra of the various target analytes). Depending on the analytes that comprise each sample mixture, investigation into the actual or potential overlaps must be carried out in order to map out these issues and mathematically determine the spectra and peaks as a function of each target analyte concentration or as a function of the presence of multiple analytes. Additionally, the Raman anti-Stokes peaks used to determine the concentration of the analyte need to be directly correlated with the concentration. In general one would require multiple peaks to generate the correlation or correlation function to the concentration.

BRIEF SUMMARY OF THE INVENTION

The invention described and claimed herein is an analyzer system for determining the identity and concentration of at least one target analyte present in a gaseous or liquid sample utilizing the Raman optical scattering effect, said analyzer system comprising a Raman anti-Stokes analyzer apparatus that utilizes HCPBG fiber to spatially confine both the pump and signal light to thereby increase the interaction length and hence the Raman anti-Stokes emission signal magnitude. The fact that the anti-Stokes light can be efficiently examined (as opposed to the Stokes radiation heretofore utilized by the prior art) allows for increased immunity to the effects of auto-fluorescence. The spontaneous Raman anti-Stokes signal is not readily used as the signature for analyte quantification due to the fact that the anti-Stokes amplitude is typically significantly (2-3 orders of magnitude) lower than the Raman Stokes signal.

Another impediment to accurate, real-time, analyte quantification alleviated by the present invention is the necessity for training sets and multivariate analysis (e.g. Principal Component Analysis and PLS), though these techniques can, if desired, still be used with the apparatus described herein. However, the necessity for such techniques is avoided for most analyte samples by several unique and advantageous features of the present invention particularly the use of known calibrant sets (compounds corresponding to the target analyte or analytes, preferably at predetermined concentrations) in the system which can be done without compromising sterility if desired or necessary. Additionally, the present invention provides the artworker with:
1. The ability to employ univariate analysis based on the spectra obtained using the apparatus of the present invention when using calibrant sets of known concentration;
2. The ability to monitor the pump light amplitude launched into the HCPBG fiber and the remaining pump light magnitude (as well as the Raman Stokes and Raman anti-Stokes emissions) exiting the fiber thereby allowing for a measure of scattering and/or absorption loss in the fiber.

These same aforementioned sets of calibrants can also be used to validate the operation of the sensor system in a cGMP or medical environment. The present invention is also advantageous in that it does not always require the use of a filter to reduce the scattering density since it generally avoids the problem of auto-fluorescence, thereby resulting in a cleaner spectrum. It should be noted however that the calibration system of the present invention can also be advantageously utilized in the case of Raman Stokes spectra.

BRIEF DESCRIPTIONS OF THE DRAWINGS

FIGS. 1-5 are illustrative of the prior art. FIGS. 6-13 are illustrative of the present invention.

FIG. 1 shows a prior art sample Raman Stokes spectrum with auto-fluorescence in the graph labeled 1. The trace labeled 2 is the Raman Stokes signal of the fluid with no processing, while trace labeled 3 is the Raman Stokes signal post ultrafiltration. The graph 4 shows the Raman Stokes signal with the auto-fluorescence subtracted out using a $5^{th}$ order polynomial fit. The trace labeled 5 is the native (unfiltered) sample and the trace labeled 6 is the signal for the ultrafiltration sample.

FIG. 2 shows a prior art Raman Stokes spectroscopy system utilizing a Teflon AF hollow core waveguide and a white light source spectrometer to measure the absorption and scatter loss in real time; this loss measurement is implemented in the concentration calculation based on the Raman Stokes signal. In this system, 200 is an 830 nm laser, 201 is a CCD based spectrograph. 202 is a spectrometer, 203 is a power meter, 204 is a white-light source, 205 is the LCOF, 206 is a dichroic beam splitter, 207 is an edge filter, and 208 is a band pass filter.

FIG. 3 shows a prior art Raman anti-Stokes flow cell and free space optical collection system as described in the aforementioned article by Dou et. al. In this figure, 300 are the sample fluid entrance and exits of the optically transparent quartz flow cell 305. The flow cell is surrounded by a gold coated "clam-shell" formed by 306 and 307. The pump laser enters the flow cell chamber 315 in the clamshell through 310 and the Raman anti-Stokes emission light is collected after the conically shaped exit 320.

DETAILED DESCRIPTION OF THE INVENTION

Figure 6:
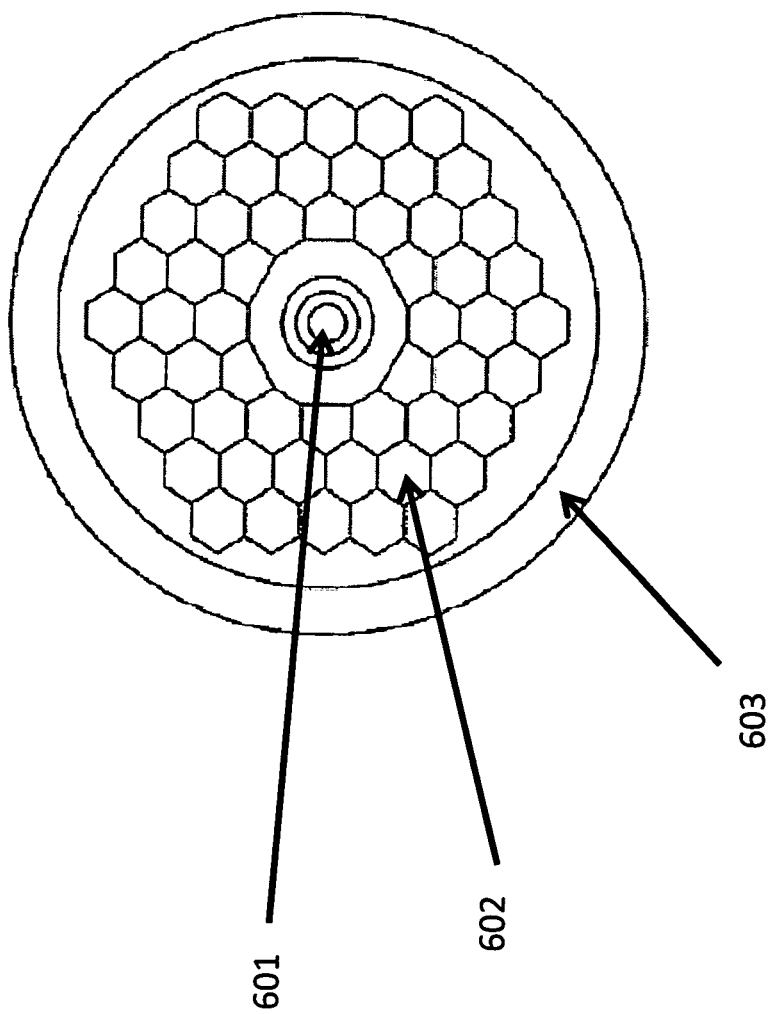
FIG. 6 shows a commercially available hollow core photonic band gap fiber suitable for use in the present invention.

FIG. 6 shows a commercially available hollow core photonic band gap fiber suitable for use in the present invention. The hollow core is shown here as 601, while the photonic band gap based cladding is shown as 602 and the solid wall surrounding the fiber is shown as 603.

Figure 7:
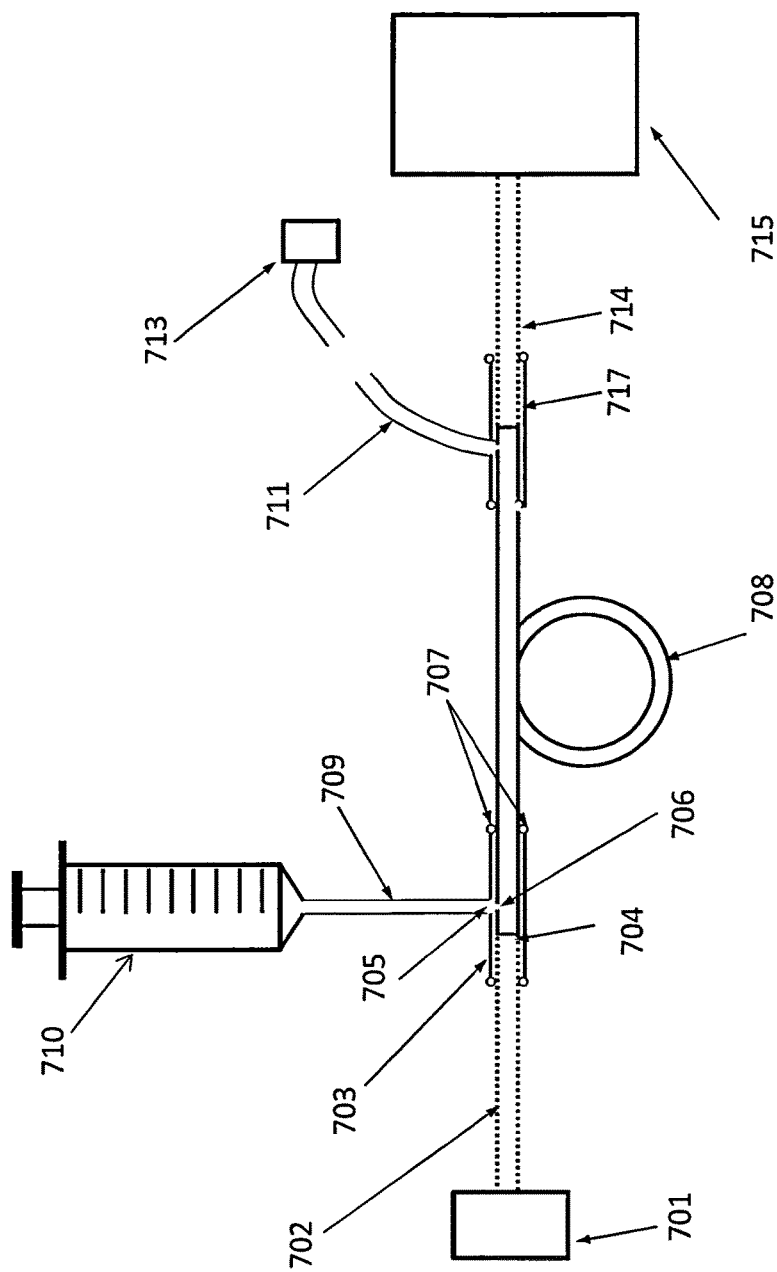
FIG. 7 shows one embodiment of the present invention.
Figure 8:
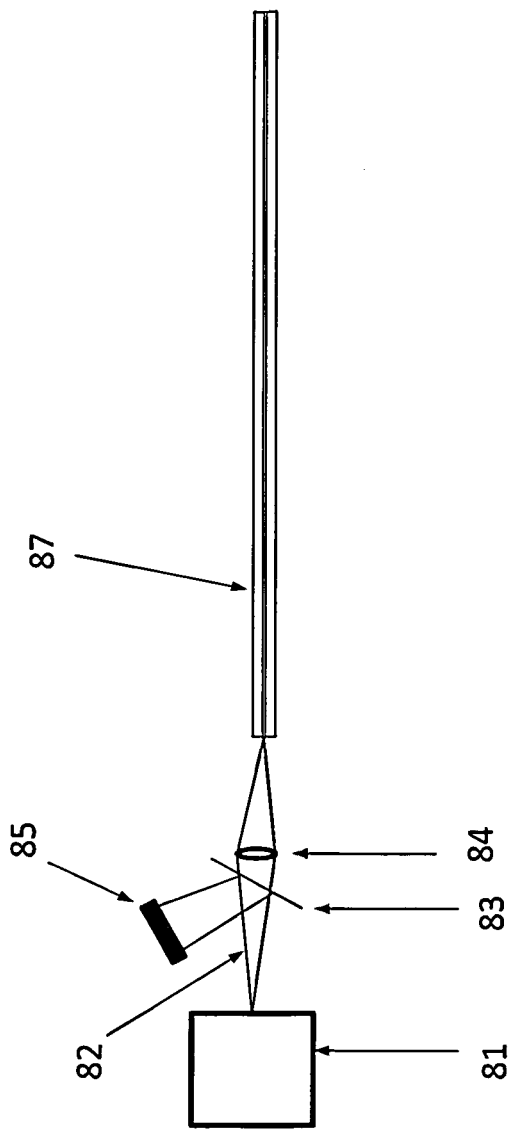
FIG. 8 depicts a pump scheme and monitoring system suitable for use in the present invention

FIG. 7 shows one embodiment of the present invention where 701 is the pump laser (excitation light) source that is described in further detail in FIG. 8. The fiber transmitting the pump light is shown as 702 while 703 is a splice protector covering the splice 704 between 702 and the HCPBG 708. The splice protector is hermetically sealed to the fibers for example by adhesive 707 which is suitably USP Class VI and gamma radiation resistant to at least 50 kGy as are preferably also the splice protector and the fiber. An inlet hole 705 through the splice protector and an inlet hole 706 through the fiber into the hollow fiber core allows a fluid sample, generally liquid (although a gaseous sample is also amenable to analysis in accordance with the present invention), to be drawn or dispensed by pump 710 through a conduit 709 such that it enters the core of the fiber. We refer to the liquid or gas to be drawn into the analyzer as a sample which can be comprised of either a single analyte or plurality of analytes to be identified and its (their) concentration(s) quantified. The hole is preferably (though not absolutely necessarily) within a few millimeters of the splice so that the entire fiber core on both sides of the hole can be readily filled with fluid thereby creating a homogenous index for optical propagation once present in the core. The fluid can also be pulled by pump 710 through the core after access from a similar splice protector 717 and access holes therein. This second access port on the exit side of the assembly can be coupled to a tube 711 so that the fluid can be drawn through a centrifuge, filtration, or ultra-filtration system 713 which, if desired, can be remotely located from the splice and hole. The exit fiber 714 is connected to the HCPBG fiber identically to that described on the input side with a splice protector and holes similarly positioned. The light from exit fiber 714 is directed to detection system 715.

The invention described in FIG. 7 allows the amplitude of the Raman anti-Stokes signal to be increased by increasing both the pump power and the interaction length without suffering the same deleterious effects of fluorescence as would be incurred by a Raman Stokes signal. In general, many parasitic signals like fluorescence will appear on the Stokes side (red shifted) of the spectrum but not on the anti-Stokes (blue shifted) side. However, even with an anti-Stokes signal it is generally desirable to minimize scattering loss, but the scattering and absorption loss can be accounted for to a first order in the present invention. Also, the use of filtered samples can significantly reduce the presence of scatterers. Any remaining scattering and absorption loss can be accounted for by noting the pump loss as it travels through the fiber before initial use; the pump loss will be both qualitatively and quantitatively indicative of the losses experienced by the Raman anti-Stokes signal. Cut back experiments (a technique well known in the art in which optical loss in which plural segments of the fiber is measured) on the fiber can be used to baseline the attenuation of the pump light in the system when filled with a liquid that does not absorb or scatter in the wavelength regime of interest (e.g.: sterile water or aqueous pH buffer solution) and monitoring of the power converted to the Raman Stokes and Raman anti-Stokes allows for a complete accounting of the input power In FIG. 7, as indicated, the excitation light source is shown as 701. For a suitable wavelength range (e.g., approximately 350 nm to 850 nm) the fiber core diameters will generally be in the range of 60 microns or less. This is further detailed in FIG. 8 which shows a wavelength stable, narrow line-width laser 81, preferably emitting in the range of 785 nm to 810 nm. This laser wavelength range is preferred in order to maintain a single- or close-to-single mode operation of a larger diameter (>40 micron) HCPBG fiber. Although ultraviolet and visible wavelength lasers can be used with the benefit of increased Raman cross-section, a downside is the increased number of tranverse modes (for a fiber of given core diameter) and therefore the potential for reduced interaction length and noise. An optimal system will excite only a fundamental mode in the HCPBG fiber, or a small number of transverse modes (e.g., less than approximately 15) such that the loss in the HCPBG fiber is deterministic and is relatively consistent (e.g. less than approximately 7% variation) in a multitude of units built the same way. The mode number can be calculated as per known procedures (see *Experimental demonstration of the frequency shift of bandgaps in photonic crystal fibers due to refractive index scaling*, G. Antonopoulos, F. Benabid, T. A. Birks, D. M. Bird, J. C. Knight, and P. St. I Russell, Opt. Express 14(7), p. 3000, 2006).

As mentioned above, one embodiment of the invention disclosed and claimed herein is shown in FIG. 7 where the excitation light transmission fiber 702 is attached to the HCPBG fiber by fusion splicing or other suitable means of producing a low loss optical connection. The splice or connection between the fibers on the entrance and the exit ends of the HCPBG fiber is protected from physical damage by cover or sleeve 703. Splice protector 703 also includes a hole through which fluid can enter and exit the HCPBG fiber. A sample can thus be pulled by a pump or syringe or other suitable dispenser 710 through the HCPBG fiber. A suitable dispenser can be any type of miniature pump as are well known in the art including printer ink-jet cartridge type devices. If the dispenser and/or pump is to be used bi-directionally, then the fluid to be analyzed can either be a calibrant injected by 710 through conduit 709 or alternatively can be a sample pulled up through the optional filtration/ultra-filtration system 713. The access holes are placed in the HCPBG fiber through the cladding into the core. This hole is optimally produced by laser drilling and preferably by $CO_2$ or $F_2$ laser drilling using known techniques where the hole is created by thermal ablation thereby also sealing the photonic band gap cladding holes simultaneously. (see *Laser drilling and routing in optical fibers and tapered micropipettes using excimer, femtosecond, and $CO_2$ lasers*, Armitage et al, Proc. SPIE 5578, 596 (2004)) The core diameter of HCPBG fiber plays a role in determining whether or not it is a single-mode waveguide. In general the fiber core diameters preferably range from about 10 microns to about 100 microns depending on the desired single mode cutoff wavelength and the photonic band gap cladding design. As previously indicated, for a suitable excitation light wavelength range (e.g., approximately 350 nm to 850 nm) the fiber core diameters will preferably be in the range of 60 microns or less. It is desirable to have both the ingress and egress holes approximately the same size as the core diameter thereby allowing the core to be filled and emptied with minimized pressure differential requirements. As mentioned before, the core can be filled by using a manual or automated dispenser 710 to pass the sample through a centrifuge or ultra-filtration system 713 or to inject a sample of known concentration of the analytes under study. (see *Recent Developments in Membrane Based Separation in Biotechnology Processes*: Review, A. S. Rathore, A. Shirke, in *Preparative Biochemistry and Biotechnology*, Vol. 41 (4), 398, 2011).

Figure 1:
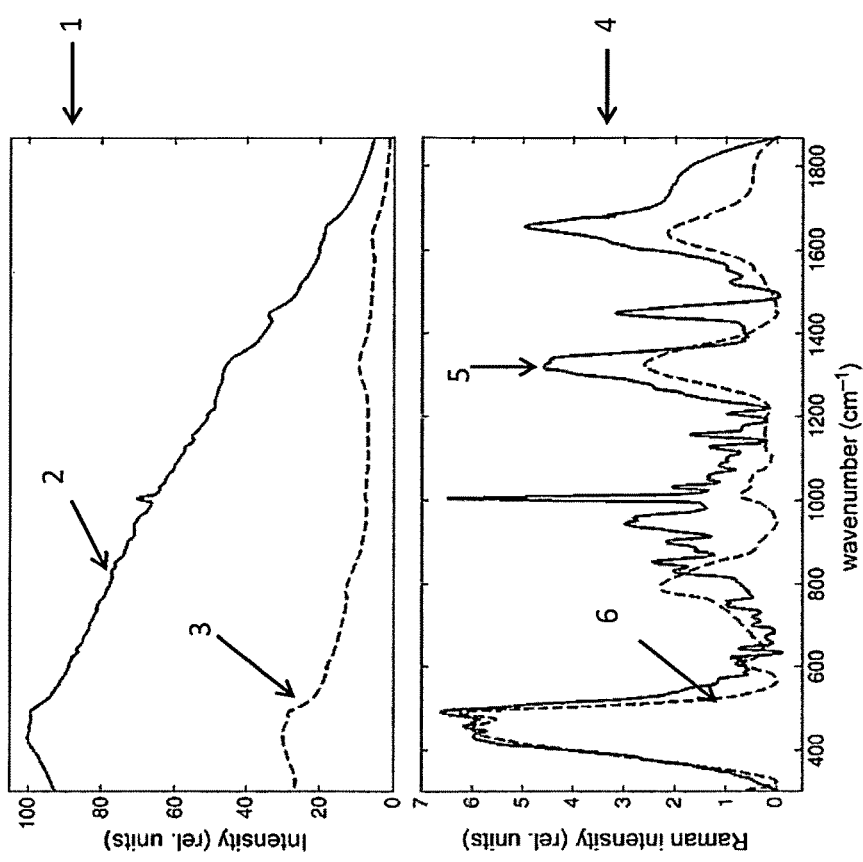
Figure 2:
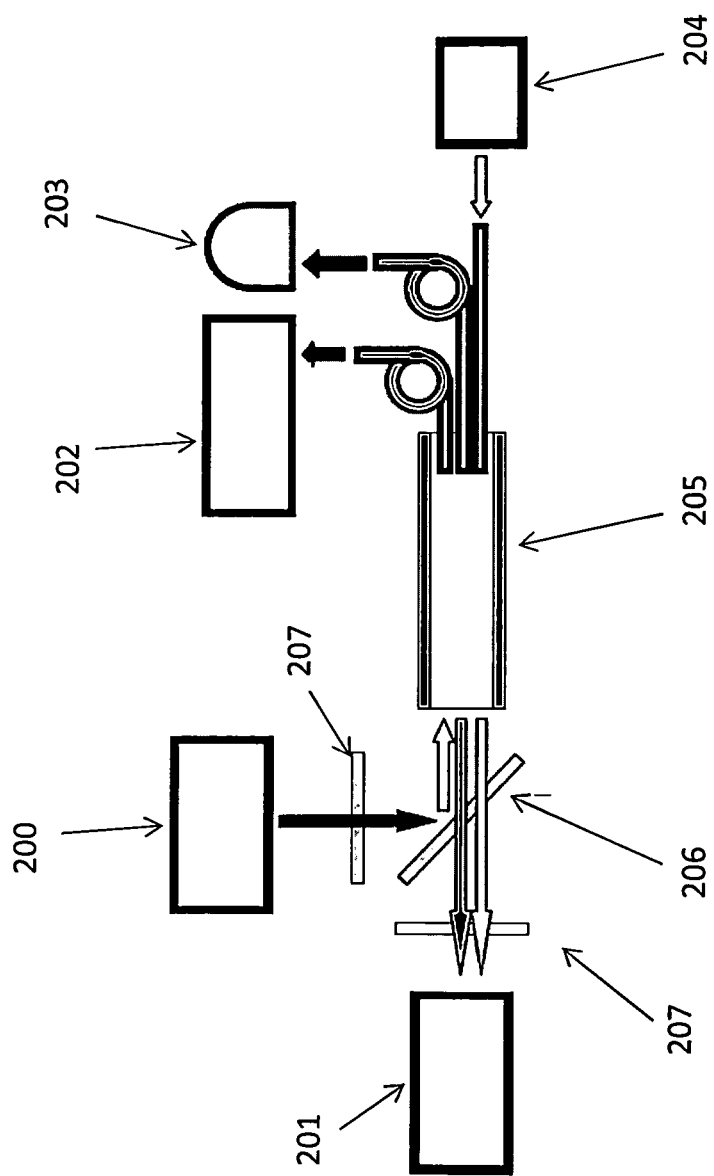
Figure 3:
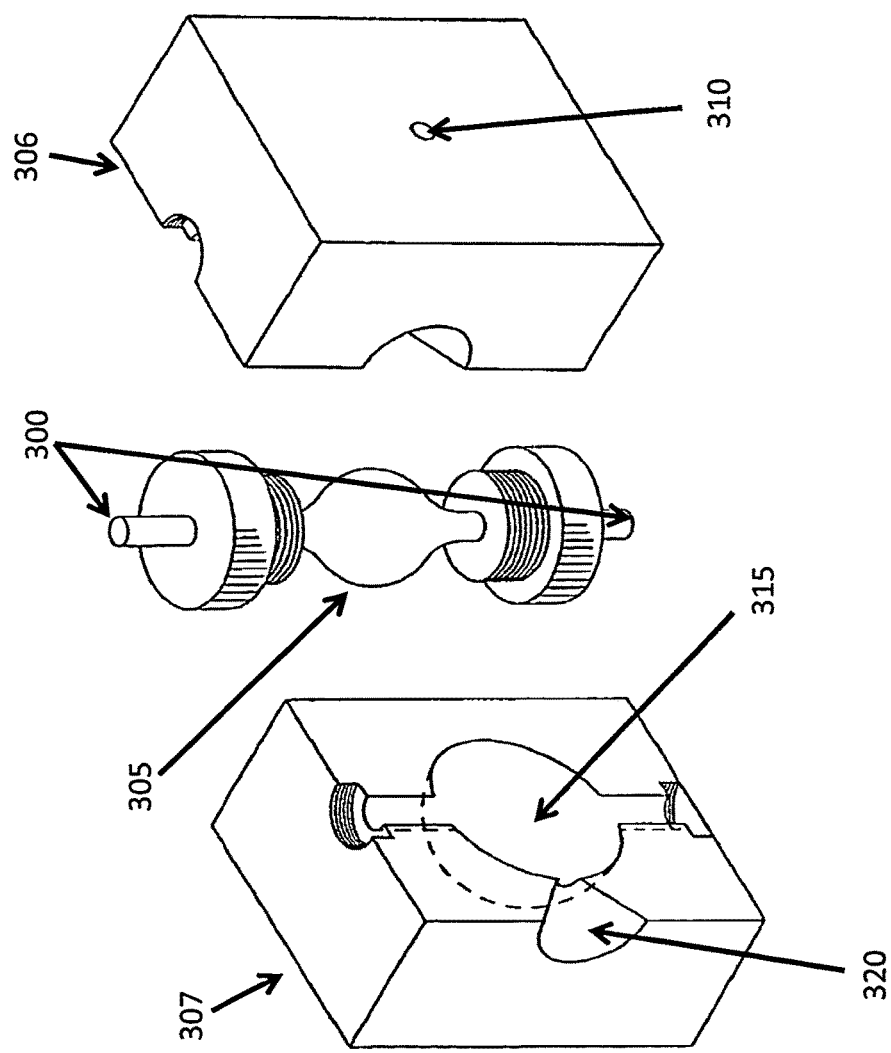
Figure 4:
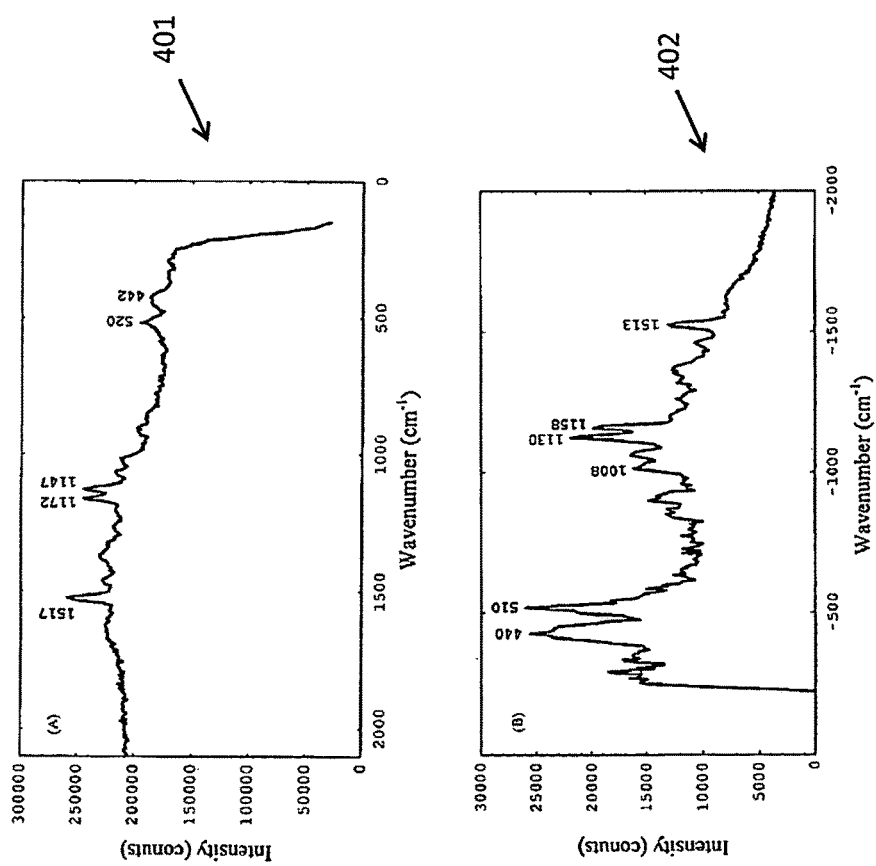
FIG. 4 shows both the Raman Stokes and Raman anti-Stokes spectrum collected using the prior art cell shown in FIG. 3. The spectrum 401 shows the Raman Stokes signal while spectrum 402 shows the anti-Stokes spectrum.
Figure 5:
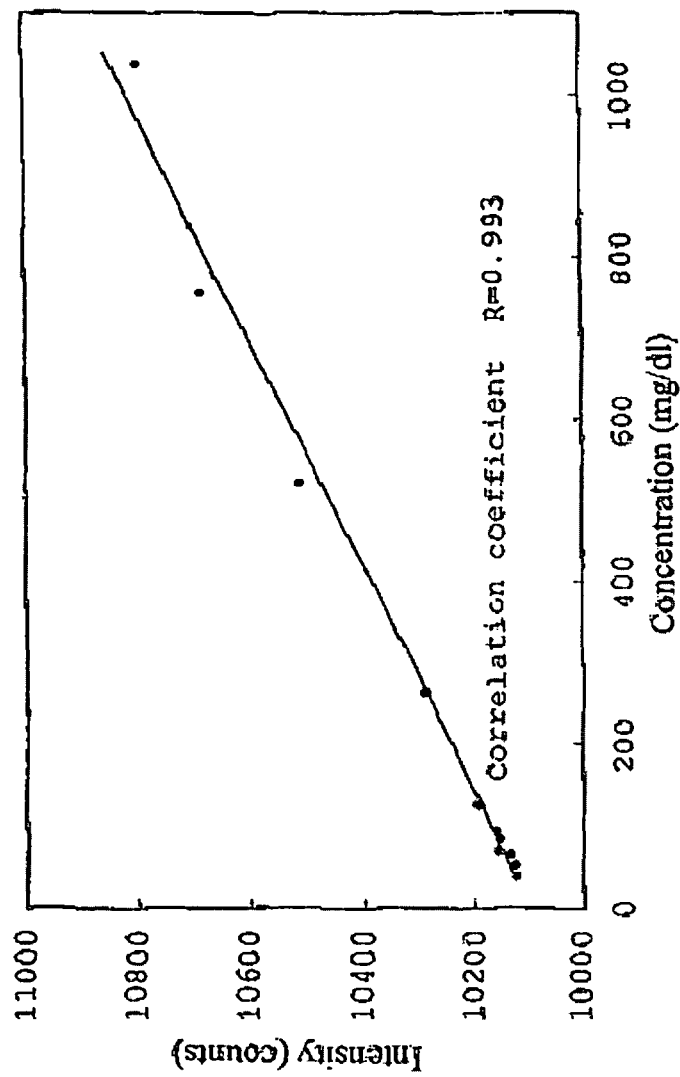
FIG. 5 shows a prior art fit and correlation between glucose concentration and a Raman anti-Stokes peak at 1130 $cm^{-1}$ with the data collected using the prior art system shown in FIG. 3.

The advantage of using an active or passive filtering system through which the sample is passed is to reduce the density of scatterers and/or absorbers in the measured sample, and thereby help provide a clean Raman spectrum such as is shown in FIG. 1. Filtering is not always required, but will generally enhance the clarity of the spectrum. An advantage of the present invention is that the use of the anti-Stokes radiation minimizes auto-fluorescence and therefore will substantially clean up the spectrum even without filtration or centrifugation. All wetted components in FIG. 7 can readily be created from USP Class VI, gamma or Beta radiation stable, and animal component derived free materials.

FIG. 8 depicts a pump (excitation light) source for use in the present invention where 81 is the laser source, and the light 82 is coupled into fiber 87 using a lens or other optical system 84. A portion of the beam is reflected using beam splitter 83 and the power (e.g. power) is measured using detector or detector/filter combination 85. Beam splitter 83 can suitably be positioned either before or after the optical system 84 depending on the details of the implementation and beam divergence and the beam splitter's optical characteristics. In FIG. 8 beam splitter 83 allows a known portion of the pump light to impinge upon a detector 85 that preferably will have a filter in front of it to ensure the fidelity of the signal. The beam can be collimated or re-focused by optics 84 and while the optics are shown after the pick off, they can equally be placed before or with the pick-off in between two lenses or similar phase changing optical elements. The pump light is subsequently coupled into a single mode or relatively low V number (see e.g., *Optical Waveguide Theory*, A. W. Snyder, J. Love, Springer, 1983) input fiber, 87, that can be fusion spliced or otherwise physically coupled to the HCPBG fiber. After passage through the HCPBG based Raman anti-Stokes analyzer the Raman Stokes light, the pump light, and the Raman anti-Stokes light are coupled into the exit fiber which is also spliced to the HCPBG as shown in FIG. 7.

Figure 9:
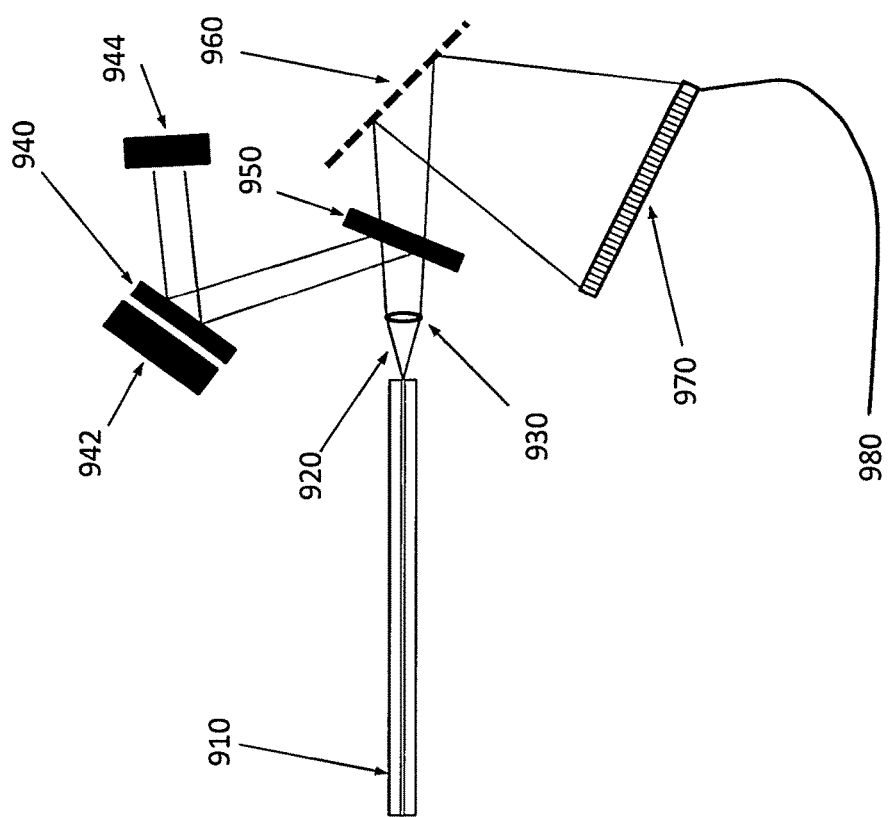
FIG. 9 shows a detection and spectral analysis system suitable for use in the present invention.

FIG. 9 shows a detection system suitable for use in the present invention. In FIG. 9 the exit fiber, 910, delivers the Raman Stokes, pump, and Raman anti-Stokes light 920 that is collimated by a lens or other system of optical elements 930 after which a dichroic beam-splitter is used to separate the pump light or the pump light and the Raman Stokes light. The separated light impinges upon a filter 940 which can let both the Raman Stokes and pump light onto detector 942, or alternatively the filter 940 can be a dichroic reflector which allows either the Raman Stokes signal or the pump light to pass and reflects the remaining pump or Raman Stokes signal to second detector 944. Since the cutback experiments on the fiber provide the fundamental loss of the fiber, and the excitation system of FIG. 8 allows one to know and monitor the amplitude of the pump light launched into the fiber, and since one also knows from the detection system of FIG. 9 the total transmitted optical power that is not either the Raman Stokes or the Raman anti-Stokes signal, one can therefore determine the absorption and scattering loss of the analyte under test. Specifically, the present invention makes it possible to account for all of the pump power that is lost in transmission through the HCPBG fiber and that is converted to the Stokes and Anti-Stokes signals. Therefore the bulk of the pump losses can be attributed to scatter and/or absorption allowing for the calculation of a loss coefficient. The spectral extent of the Raman Stokes and Raman anti-Stokes signals of interest are on the order of 50 nm to the red shifted and blue shifted sides of the pump wavelength, respectively, and the scattering and absorption functions will not generally change value significantly in this region. In FIG. 9 the exit fiber is shown as 910 and light exiting the HPBG fiber couples directly into the exit fiber. Light 920 from the fiber is collimated by lens or optical system 930. Dichroic beam-splitter 950 sends pump and Raman Stokes light and remaining pump light to band-pass filter/detector pair 940/945 where the pump light amplitude is passed and measured and the Raman Stokes light reflected. The Raman Stokes amplitude is measured at detector 944. The remaining light, i.e., the Raman anti-Stokes signal, impinges on dispersive element (e.g. a ruled or holographic grating) 960 and is dispersed to detector array or CCD 970. The resultant electrical signal is carried to a data signal processing unit or other similar computer system by cable 980. The entire Raman anti-Stokes spectrum can now be examined for the spectral signatures of the analytes under study. This allows the spectral features of the analyte's Raman anti-Stokes signal to be fully analyzed. If, as is generally the case in bioprocessing, the basic make-up of the analyte containing media and analytes are known, it is feasible to create a map of the spectral peaks of interest. This map can be used in conjunction with the data from 980 and aforementioned data signal processing system to identify the analyte concentrations using univariate analysis or peak fitting/area analysis.

Figure 10:
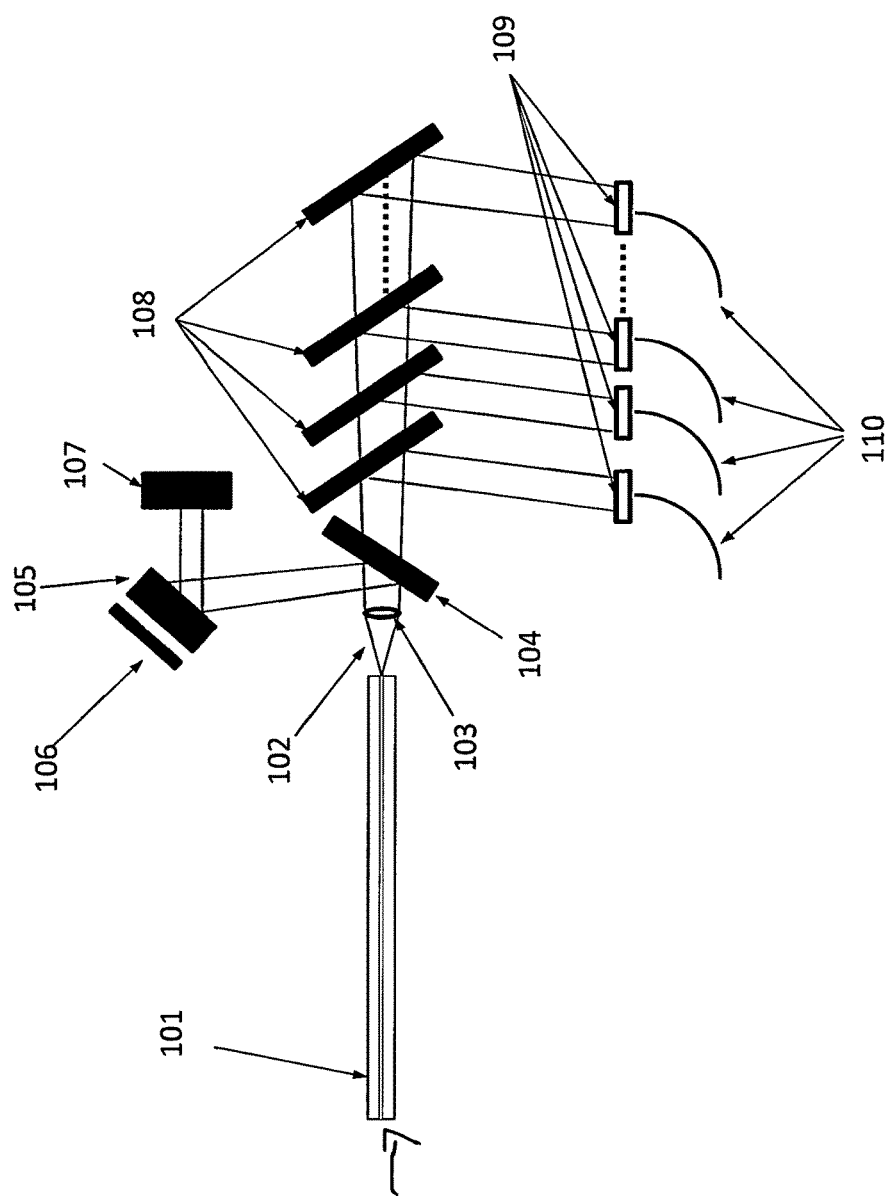
FIG. 10 shows an alternative detection system based on spectral peak detection suitable for use in the present invention.

FIG. 10 shows a detection system where 101 is the exit fiber and the remaining pump, Raman Stokes, and Raman anti-Stokes light beam 102 from the exit fiber is collimated by lenses or optical system 103. The light beam hits dichroic beam splitter 104 and the pump and Raman Stokes light is sent to dichroic beam splitter 105 which causes the pump light to hit filtered detector 106 and Raman Stokes light to hit band pass optically filtered photo detector 107 thus allowing analysis of scattering loss in the system with the pump power as the reference. A dichroic beam-splitter array is depicted by 108 where Raman anti-Stokes spectral regions of interest transmitted by 104 are split off and sent to a discrete optically filtered detector array 109. The resulting electrical signals are carried by a set of cables or wires 110 to a data signal processing system such as for example a PC type computer. The dichroic elements are chosen to correspond to the known spectral features of the sample under test. For samples comprised of a small number (<~15) of analytes where the amplitudes of spectral peaks have been found to directly correlate to concentration have already been mapped out, this detection system is especially simple and cost effective.

Figure 11:
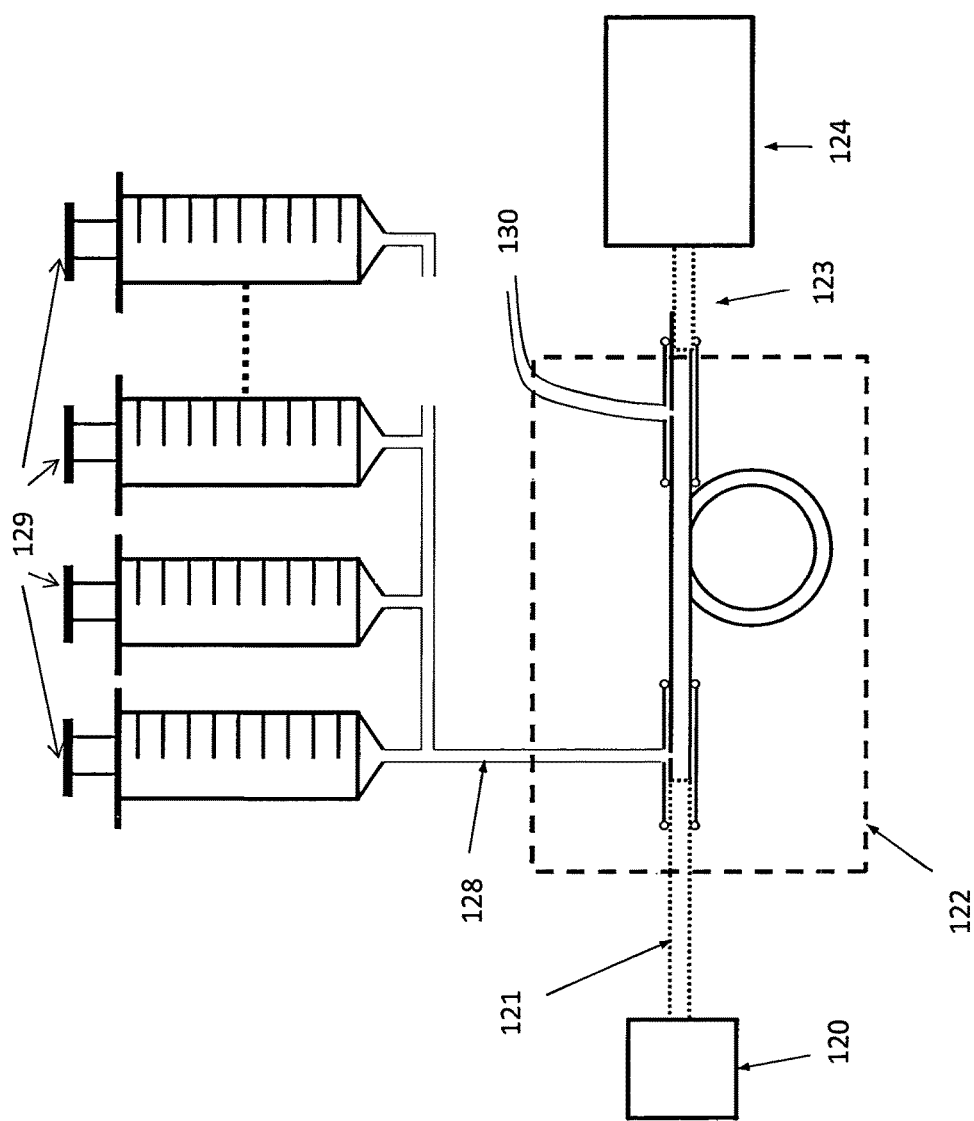
FIG. 11 depicts an embodiment of the present invention that allows for calibration and validation of the system

FIG. 11 shows an embodiment of the present invention that allows for the use of multiple calibrants or multiple concentrations of one analyte or any combination thereof such that the system's base-line response can be established. Specifically, if it is known that certain analytes will be present in the sample it is possible to take into account any cross sensitivities or spectral peak overlaps by having available known concentrations of the analyte or admixtures/combinations of multiple known concentrations of analytes available such that the spectrum can be taken of the system that will be used to quantitatively analyze the samples under test. For example of it is known a priori that the sample will mainly consist of water, buffering systems for pH stabilization (e.g.: borate or phosphate based solutions), glucose, lactose, urea, glutamine, glutamate, and some specific additives to help cell growth as is commonly found in buffered media during cell growth processes, one can map out the maximum and minimum concentrations and provide pre-mixed, sterile samples contained in 129 as shown in FIG. 11 such that the system response of the analyzer can be automatically pre-calibrated. Specifically, the peaks can be identified and amplitudes correlated to analyte concentration and cross-sensitivities can be also be mapped out. This can also be done in a similar fashion for blood, food/beverage, chemistry, and wastewater analysis or any sample where the sample constituents are known to a reasonable degree of certainty in advance. Subsequently, samples can be taken in real time and the spectrum analyzed using univariate analysis to quantitatively and accurately yield the concentrations of the analytes that make up the sample. (see *Data, models, and statistical analysis*, A. Cooper, Tony J. Weekes, Rowman & Littlefield, 1983, ISBN 0389203831). Additionally, analyte samples 129 can also be used in a cGMP setting to allow validation of the system. (see *GAMP5, A Risk-Based Approach to Compliant GxP, Computerized Systems*, 2007, ISPE.) In the present invention, the work of creating training sets for use in multi-variate analysis (e.g. PLS or PCA) can be optionally replaced with a more deterministic method of systematically creating calibrants. The system described herein can be used with multi-variate analysis as well. FIG. 11 depicts an embodiment of the present invention that allows for calibration and validation of the system. The excitation light optics 120 connects to the HCPBG optical fiber system 122 through the excitation fiber 121 and travels through the exit fiber 123 to the detection system 124. The fluid can be drawn into or pushed out of the core of HCPBG fiber through inlet 130. Calibration or validation liquids can be introduced into the core of the HCPBG using dispensing units 129 or subsequently withdrawn into empty dispensers. These units, 129, are connected to a common conduit 128 to enter the HCPBG optical fiber system 122.

Figure 12:
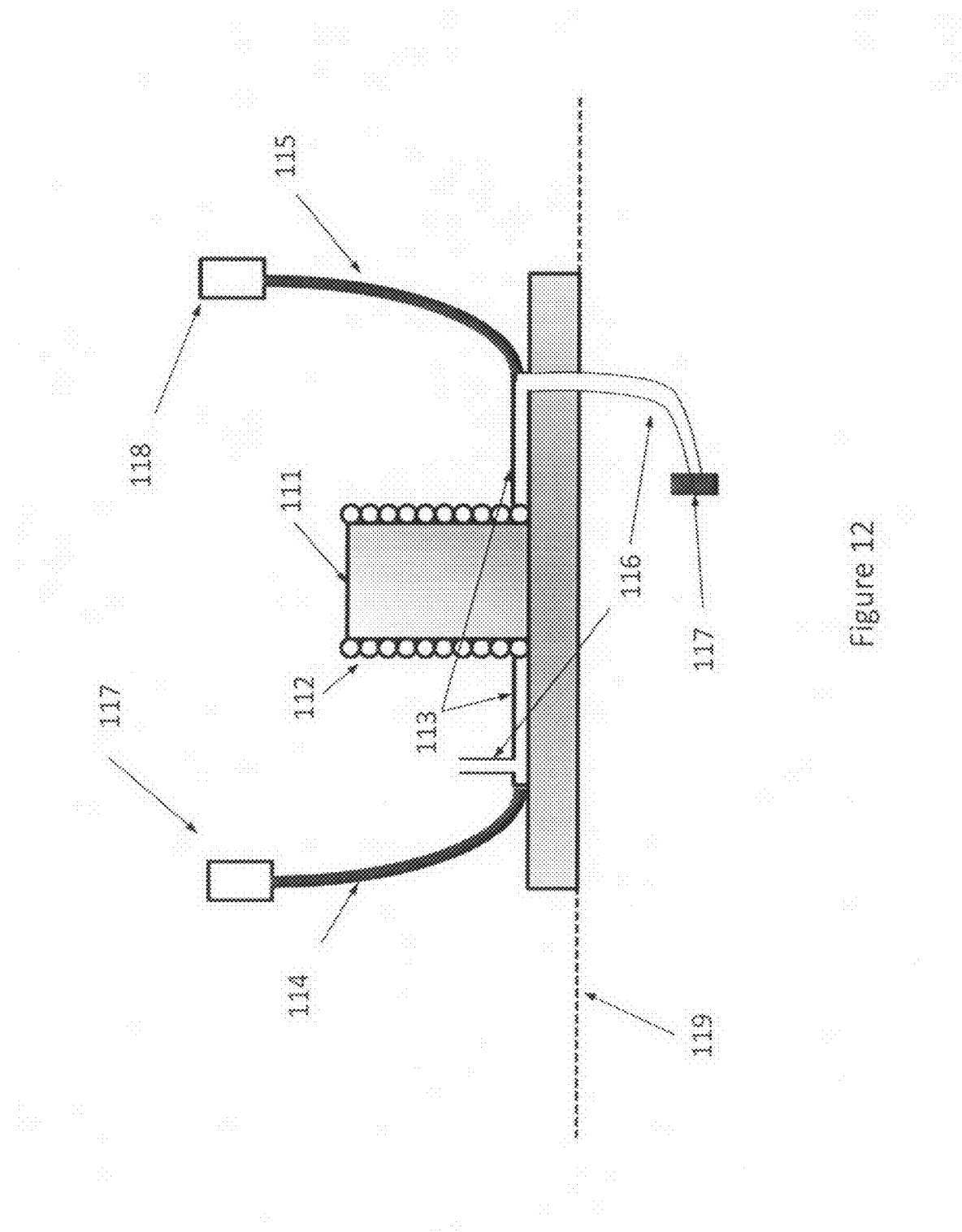
FIG. 12 illustrates an embodiment of the invention specifically adapted for bioprocess monitoring

FIG. 12 depicts an embodiment of the present invention that is particularly well suited for use in bio-processing applications such as in a bioreactor, a mixer for production of media or buffers or similar products, or in a bioprocessing down-stream processing skid. In this application, the very small bend radius (typically <1 cm) of HCPBG fiber 112 can be exploited by wrapping it around a small diameter mandrel 111 preferably constructed of USP Class VI ultra-low density polyethylene or composite material such as is described in co-pending, commonly assigned U.S. patent application Ser. No. 13/385,100. The HCPBG fiber 112 is wrapped around a solid disk and mandrel 111 that can be attached to the wall of a polymeric bioreactor vessel 119. The pump entrance and exit optics 118 is attached to the input fiber 114 and the detection system 118 is connected by the exit fiber 115. The fluid sample enters and exits the HCPBG fiber through ports 116. If desired the fluid can be pulled into the core of the HCPBG fiber through a filtration or ultra-filtration system 117 which is attached to excitation fiber 114. The fluid introduction path where the splice and splice protection occurs (between 114 and 112) is shown here as 113. The exit fiber is shown as 115 connected to detection system 118. The bioreactor, mixer, or other system is shown here as having a flexible polymer wall 119, alternatively this can also be a wall that comprises part of a plastic vessel that this embodiment of the invention is bonded to. In general practice, the inner layer of this wall in a single-use bioreactor or mixer is comprised of ultra-low density polyethylene or similar high surface energy polymer (>20 dynes/cm.) and can be fusibly sealed to the base of mandrel 111. Fluid port 116 on the exit side is shown leading to the inside of the container and is terminated by a filtration or ultra-filtration system 117. A similar system can be created that sits outside the system (e.g.: bioreactor, mixer, downstream processing system) where the fluid sample input port 117 leads to a pump or sampling system followed by a centrifuge, or other filtration system that has already taken a sample and processed it to remove scatterers thereby leaving the fluid with a quality similar to that of a supernatant liquid in that the chemical composition is complete, but the precipitant or other solids have been removed. With the use of ultra-filtration and minimized scattering of the pump and signal beams, the clarity of the spectrum approaches that seen by Meneghini et al in the Raman Stokes spectrum of ethanol where the effects of scatterers and auto-fluorescence were both minimal. Therefore the quantitative analysis of the spectrum becomes similarly straightforward and the need to keep track of the pump losses is eliminated.

Figure 13:
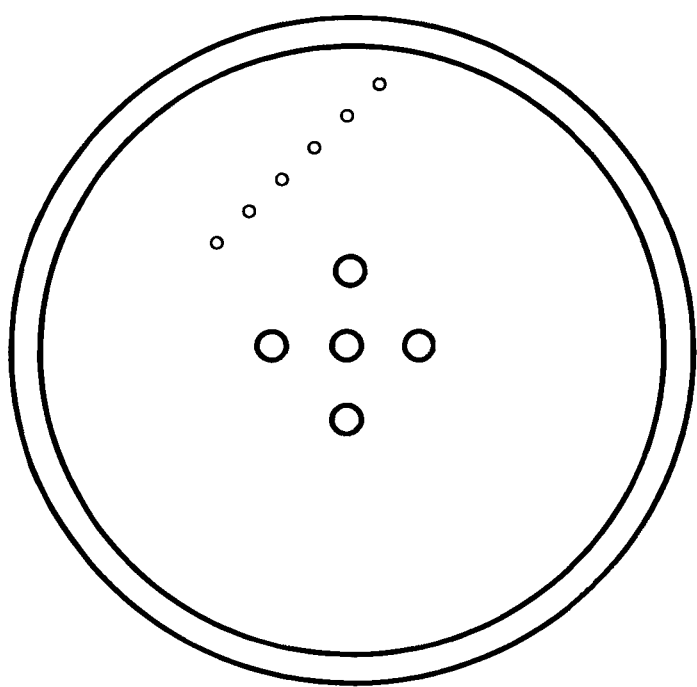
FIG. 13 depicts a custom HCPBG fiber having more than one core.

FIG. 13 depicts a custom HCPBG fiber having at least two cores. For simple systems of analytes, it is possible as shown in FIG. 13, to create HCPBG fibers with multiple hollow cores. Some of these cores can be pre-filled with calibrants fluids of known and certified/validated analyte concentration such that the system is pre-configured and ready to use. The only operational change in the system is the addition of the ability to switch the entrance fiber and exit fiber light to and from the particular fiber of interest respectively. This switching technology has existed commercially since the telecom "boom" of the 1990s and now is commercially available in many formats.

Another embodiment of the present invention immediately applicable to biotech/bioprocessing utilizes two or more HCPBG fiber channels in parallel along a mandrel thereby enabling one to switch the optical signal output with a coupler from sample to reference calibrant in real-time, thereby eliminating the need to run the sample and calibrant through the same physical path, and mitigating customer concerns about flushing any of the calibrant through the filter into the bioreactor.

We claim:

1. An analyzer system for determining the identity and concentration of at least one target analyte present in a liquid sample from a bioprocess utilizing anti-Stokes Raman optical scattering effect, said analyzer system comprising:
   i) a laser light source emitting light having a wavelength in the ultraviolet to near infrared spectral region which generates Raman anti-Stokes emissions when incident on said analyte;
   ii) a hollow core photonic band-gap fiber optically connected to said light source, said fiber including a first inlet configured to permit introduction of an analyte containing the liquid sample from the bioprocess into the fiber;
   iii) a plurality of reference calibrants comprising multiple analytes and/or multiple concentrations of analyte corresponding to an analyte in the sample;
   iv) a second inlet permitting introduction of said calibrant into the fiber;
   v) a spectral analysis system optically coupled to said fiber and configured to
      (i) detect and measure spontaneously scattered Raman-shifted anti-Stokes emission signals received from said fiber and to derive the Raman anti-Stokes spectral peaks and/or spectra of said calibrants and said target analyte present in the liquid sample, and to utilize the amplitudes of spontaneously scattered Raman-shifted anti-Stokes spectral peaks and/or spectra of the plurality of calibrants and the target analyte in univariate analysis to thereby quantitatively yield the concentration of the target analyte in the liquid sample, and
      (ii) use the spontaneously scattered Raman-shifted anti-Stokes spectral peaks and/or spectra of the plurality of calibrants to establish a baseline response of the analysis system to account for cross sensitivities or spectral peak overlaps of analytes in the liquid sample; and
   vi) an outlet for expelling the analyte and/or a plurality of calibrants from the fiber.

2. The system of claim 1 wherein the fiber has multiple hollow channels.

3. The system of claim 1 further comprising two or more hollow core photonic band-gap fibers wound in parallel along a mandrel and a coupler which switches optical signal output from one fiber to the other in real-time.

4. The system of claim 1 wherein a single hollow core photonic band-gap fiber having two or more parallel channels is wound along a mandrel, and further comprising a coupler configured to switch optical signal output from one fiber channel to the other in real- time.

5. The system of claim 1 wherein the spectral analysis system comprises an optical element selected from the group of filters, dispersive elements, a detector array, a CCD, and combinations thereof.

6. The system of claim 1 wherein the spectral analysis system comprises at least one optically filtered photo-detector and/or optically filtered photo-detector array.

7. The system of claim 1 further comprising a sample filtration system configured to pass the liquid sample before being introduced into the hollow core photonic band-gap fiber.

8. The system of claim 7 wherein the filtration system comprises a centrifuge and/or an ultra-filtration system.

9. The system of claim 1 wherein the plurality of reference calibrants is sterile.

10. The system of claim 1 wherein said liquid sample contains a plurality of analytes.

11. The system of claim 10 wherein the liquid sample contains known concentrations of said analytes.

12. The system of claim 1 further comprising a monitor configured to measure the amplitude of the light source before it is introduced into the hollow core photonic band gap fiber.

13. The system of claim 1 wherein the spectral analysis system further comprises a monitor which measures the magnitude of the pump light signal, Raman Stokes emission signals, and the Raman anti-Stokes emission signals after exit from the photonic band gap fiber and thereby determines the scattering and/or absorption loss.

14. The system of claim 1 wherein the spectral analysis system is further configured to use multi-variate analysis of the Raman anti-Stokes spectra and corresponding training sets in determining the concentration of the analyte or analytes in said liquid sample.

15. The system of claim 1 wherein said laser light source emits light in the range of approximately 350 to 850 nm.

16. The system of claim 13 wherein said laser light source emits light in the range of 785 to 810 nm.

17. A system for the determination of the concentration of at least one target analyte present in a liquid sample using Raman anti-Stokes radiation spectroscopy said system comprising:
   a. a laser pump light source for emitting light in the ultraviolet to near infrared spectral region;
   b. an inlet for permitting said laser light into a hollow core photonic band gap fiber, said fiber configured to operate in a fundamental mode or a limited number of modes;
   c. said fiber having an inlet port allowing a plurality of reference calibrants comprising multiple analytes and/or multiple concentrations of analyte to be introduced into the core of the fiber, and an additional port permitting the sample to be introduced into the core of said fiber;
   d. a spectral analysis system comprising at least one filter and/or dispersive element and a detector array or CCD, wherein the spectral analysis system is optically coupled to the fiber and configured to
      (i) detect and measure spontaneously scattered Raman-shifted anti-Stokes emission signals received from the fiber and to derive the Raman anti-Stokes spectral peaks and/or spectra of the plurality of calibrants and the target analyte present in the liquid sample, and to utilize the amplitudes of spontaneously scattered Raman-shifted anti-Stokes spectral peaks and/or spectra of the plurality of calibrants and the target analyte in univariate analysis to quantitatively yield the concentration of the target analyte in the liquid sample, and
      (ii) use the spontaneously scattered Raman-shifted anti-Stokes spectral peaks and/or spectra of the plurality of calibrants to establish a baseline response of the analysis system to account for cross sensitivities or spectral peak overlaps of analytes in the liquid sample; and
   e. a coupling for optically coupling components a) and d) to the core of said fiber.

18. The system of claim 17 wherein the laser light source includes an amplitude monitor.

19. The system of claim 18, wherein the spectral analysis system is configured to monitor the amplitudes of the signals that exit the hollow core photonic bandgap fiber and account for scattering and/or absorption loss of the Raman anti-Stokes signal.

20. The system of claim 17 further comprising a filtration system configured to pass the liquid sample before being introduced into the hollow core photonic band-gap fiber.

21. The system of claim 17 wherein at least one of the hollow core photonic band-gap fiber, the calibrant inlet port, the plurality of calibrants, the sample inlet port, and the filter is a single-use component.

22. The system of claim 21 wherein the single-use component is integrated into a single-use bioprocessing container.

23. The system of claim 17, wherein the system comprises polymeric components which are USP Class VI, animal component derived free, and stable under sterilization with gamma or beta radiation.

24. The system of claim 17, wherein said system is connected to a bioprocessing container.

25. The system of claim 17 wherein the target analyte includes at least one of glucose, glutamine, glutamate, lactate, and ammonia.

26. The system of claim 17, wherein the target analyte includes at least one of enzymes, kinases, monoclonal antibodies, and virus-like particles or bioprocess additives.

27. The system of claim 17, wherein the hollow core photonic bandgap fiber is wound around a mandrel.

28. The system of claim 17, wherein the laser pump light source is a DFB semiconductor diode laser or external cavity diode laser.

29. The system of claim 17 further comprising narrow-band optical transmission filters whose center wavelength corresponds to the Raman anti-Stokes spectral peak of the target analyte through which the laser light passes prior to impinging upon photodiodes.

30. The system of claim 17 wherein the dispersive element is a ruled or holographic grating.

31. The system of claim 17 wherein the fiber has multiple hollow cores.

32. The system of claim 17 further comprising at least a second parallel hollow core photonic band gap fiber, all said fibers being wound along a mandrel and a coupler optically connected to all said fibers which coupler includes means to switch the optical signal output from that of the sample to that of the plurality of reference calibrants in real-time.

33. The system of claim 1, wherein the hollow core photonic bandgap fiber does not contain a surface enhancement material.

34. The system of claim 1, further comprising an interface configured to interface with a bioprocessing system.

35. The system of claim 1, wherein the laser light source comprises a DFB semiconductor diode laser or external cavity diode laser.

36. The system of claim 17, wherein the hollow core photonic bandgap fiber does not contain a surface enhancement material.

37. The system of claim 17, further comprising an interface configured to interface with a bioprocessing system.

38. The system of claim 1, wherein said laser light source emits light in the range of 700 to 900 nm.

39. The system of claim 10, wherein the spectral analysis system is configured to detect the Raman anti-Stokes spectral peaks and/or spectra of the plurality of analytes.

40. The system of claim 1, wherein the laser light source emits light having a wavelength in the near infrared spectral region.

41. The system of claim 17, wherein the laser pump light source emits light having a wavelength in the near infrared spectral region.

\* \* \* \* \*